US012629520B2

(12) United States Patent
Yamazaki

(10) Patent No.: US 12,629,520 B2
(45) Date of Patent: May 19, 2026

(54) BEAUTY DEVICE AND CONTROL METHOD THEREFOR

(71) Applicant: YA-MAN LTD., Tokyo (JP)

(72) Inventor: Iwao Yamazaki, Tokyo (JP)

(73) Assignee: YA-MAN LTD., Tokyo (JP)

( * ) Notice: Subject to any disclaimer, the term of this patent is extended or adjusted under 35 U.S.C. 154(b) by 550 days.

(21) Appl. No.: 17/431,435

(22) PCT Filed: Mar. 16, 2020

(86) PCT No.: PCT/JP2020/011399
§ 371 (c)(1),
(2) Date: Jan. 30, 2022

(87) PCT Pub. No.: WO2020/196012
PCT Pub. Date: Oct. 1, 2020

(65) Prior Publication Data
US 2022/0305261 A1     Sep. 29, 2022

(30) Foreign Application Priority Data

Mar. 25, 2019    (JP) ................................ 2019-056053

(51) Int. Cl.
*A61N 1/36*        (2006.01)
*A61F 7/00*        (2006.01)
*A61N 1/32*        (2006.01)

(52) U.S. Cl.
CPC .......... *A61N 1/36031* (2017.08); *A61F 7/007* (2013.01); *A61N 1/328* (2013.01); *A61N 1/36034* (2017.08); *A61F 2007/0052* (2013.01)

(58) Field of Classification Search
CPC ................ A61N 1/36031; A61N 1/328; A61N 1/36034; A61F 7/007; A61F 2007/0052;
(Continued)

(56) References Cited

U.S. PATENT DOCUMENTS 3,851,651 A * 12/1974 Icenbice, Jr. ...... A61N 1/36034
                                                              377/122
2004/0073274 A1* 4/2004 Cook ..................... A61N 1/328
                                                              607/145
(Continued)

FOREIGN PATENT DOCUMENTS

CN          108463201 A      8/2018
JP          H08112362 A      5/1996
(Continued)

OTHER PUBLICATIONS

Apcp.csp.org.uk, "A Guide to the Use of Electrical Stimulation in Paediatric Neurodisability;" https://apcp.csp.org.uk/content/guide-use-electrical-stimulation-paediatric-neurodisability, accessed Aug. 25, 2025 (Year: 2025).*

(Continued)

*Primary Examiner* — Jennifer Pitrak McDonald
*Assistant Examiner* — Christopher J Mutchler
(74) *Attorney, Agent, or Firm* — Bayramoglu Law Offices LLC

(57)                    ABSTRACT

A beauty device applies an alternating current to the skin surface of a user and changes a frequency while keeping a voltage or the like constant in order to adjust the degree of a bodily sensation. A beauty device includes: an electrode portion that includes two or more electrodes and applies the alternating current between the electrodes; a frequency setting portion that sets the frequency of the alternating current either in multiple stages of three or more stages or steplessly; a sensitivity adjusting portion that adjusts the degree of a bodily sensation of the user; and an alternating current generating portion that outputs the set frequency; in which the frequency setting portion sets the frequency based on the adjustment of the sensitivity adjusting portion to adjust the degree of a bodily sensation.

2 Claims, 5 Drawing Sheets

New technology: Change frequency while keeping the voltage constant low                                                    high

(58) Field of Classification Search
   CPC ...... A61F 2007/0075; A61F 2007/0087; A61F 2007/0088; A61F 2007/0071; A61B 5/0531
   See application file for complete search history.

(56) References Cited

U.S. PATENT DOCUMENTS

| | | | | |
|---|---|---|---|---|
| 2013/0073001 A1* | 3/2013 | Campbell | ............ | A61N 5/0616 607/88 |
| 2016/0089537 A1 | 3/2016 | Yamazaki | | |
| 2017/0036019 A1* | 2/2017 | Matsushita | ........ | A61N 1/36034 |
| 2019/0329035 A1* | 10/2019 | Park | ................... | A61N 1/36034 |
| 2020/0330754 A1* | 10/2020 | Kim | ....................... | A61N 1/328 |

FOREIGN PATENT DOCUMENTS

| | | | |
|---|---|---|---|
| JP | 4057558 | B2 | 3/2008 |
| JP | 2013059556 | A | 4/2013 |
| JP | 2014113272 | A | 6/2014 |
| JP | 201777305 | A | 4/2017 |
| JP | 6212608 | B2 | 10/2017 |
| JP | 2018130576 | A | 8/2018 |
| JP | 2018521804 | A | 8/2018 |
| JP | 2018139780 | * | 9/2018 |
| JP | 2018139780 | A | 9/2018 |
| JP | 2018149343 | A | 9/2018 |
| JP | 2019000212 | A | 1/2019 |
| KR | 20040050156 | A | 6/2004 |
| KR | 100806318 | B1 | 2/2008 |
| KR | 101122051 | B1 * | 3/2012 |
| KR | 20190107816 | A * | 3/2018 |
| WO | 2017023132 | A1 | 2/2017 |
| WO | 2018054922 | A1 | 3/2018 |
| WO | WO-2019185168 | A1 * | 10/2019 |

OTHER PUBLICATIONS

G. Hsu et al., "Cutaneous sensation of electrical stimulation waveforms;" Brain Stimulation vol. 14, Issue 3, May-Jun. 2021, pp. 693-702 (Year: 2021).*

* cited by examiner

Conventional: Change the voltage
to increase the output

New technology: Change frequency
while keeping the voltage constant low                                        high

BEAUTY DEVICE AND CONTROL METHOD THEREFOR

CROSS REFERENCE TO THE RELATED APPLICATIONS

This application is the national phase entry of International Application No. PCT/JP2020/011399, filed on Mar. 16, 2020, which is based upon and claims priority to Japanese Patent Application No. 2019-056053, filed on Mar. 25, 2019, the entire contents of which are incorporated herein by reference.

TECHNICAL FIELD

The present invention relates to a beauty device which applies an alternating current to provide electrical stimulation to the skin surface of a user, and particularly to a control method related to the degree of a bodily sensation.

BACKGROUND

Beauty devices which apply a current of a predetermined frequency are conventionally known. A beauty device which provides electrical muscle stimulation called EMS (Electrical Muscle Stimulation) and a RF beauty device which provides a hyperthermic effect by use of a higher frequency band to enhance skin firmness and elasticity are provided. In the EMS, electrical stimulation is provided at frequencies of several Hz to several kHz to skin so as to cause muscle contraction and to thereby exercise muscles, and thus it is possible to improve sagging. In the RF, high frequency waves of several hundred kHz or more are used to warm the inside of skin, and thus it is possible to improve wrinkles and firmness.

Patent literature 1 proposes a technique for preventing local heat from being provided to skin in a high frequency beauty treatment device. The present literature discloses that the high frequency beauty treatment device includes a potable housing, parallel electrodes which are spaced a predetermined distance on a tip portion of the housing and which have a treatment surface for making contact with the skin of a person to be treated and a first power supply portion which is incorporated in the housing and which supplies a high frequency current to the pair of parallel electrodes.

Patent literature 2 proposes a muscle training device which can carry a large current into the body of a user without making the user feel an excessive pain. In the present device, a control portion receives an input of an electrical stimulation signal, that is, the magnitude of a current value from the user through an operation portion to receive an instruction to increase the magnitude of the electrical stimulation signal, accesses a storage portion to reference current frequency correlation data, obtains a frequency corresponding to the magnitude of the electrical stimulation signal specified by the user and outputs the magnitude of the electrical stimulation signal and the frequency to an electrical stimulation output portion. It is disclosed that the electrical stimulation output portion generates the electrical stimulation signal by receiving an input of data from the control portion and outputs it to individual electrodes.

Patent literature 3 proposes an interference low frequency therapy device which can perform satisfactory energization treatment by adjusting the depth of a position in the affected part of a human body where interference waves are generated. In the interference low frequency therapy device, a control portion has a frequency setting function to be able to change the depth of the position in the private part of the human body where the interference waves are generated by arbitrarily changing the frequencies of two intermediate frequency currents.

Although it is known in conventional techniques that frequencies can be changed, the purpose thereof is to switch between a relatively low frequency band for providing electrical stimulation and a relatively high frequency band for providing a hyperthermic effect so as to realize different beauty effects.

Although patent literature 2 discloses, for example, that the electrical stimulation signal and the frequency are directly proportional to each other, the frequency used falls in a range of several Hz to several kHz, and thus a high frequency cannot be technically handled. The magnitude of the electrical stimulation signal is a current value and is not adjusted only by the frequency, and the current value needs to be adjusted.

In patent literature 3, since the two intermediate frequency currents are arbitrarily set to change the depth of the position where the interference waves are generated, a frequency setting control and an intensity setting control are provided, and the intensity is adjusted by the magnitude of an interference wave carrier current. Hence, the intensity is not adjusted by the frequency, and thus a complicated configuration is needed.

CITATION LIST

Patent Literature

Patent Literature 1: Japanese Patent No. 6212608
Patent Literature 2: Japanese Patent No. 4057558
Patent Literature 3: Japanese Unexamined Patent Application Publication No. 8-112362

SUMMARY

Technical Problem

Although in the conventional techniques, an electricity providing beauty device uses a voltage or a current to adjust a bodily sensation, for example, the following problems occur. When a voltage or the like is increased, the degree of tingling stimulation is increased to cause discomfort, and thus the beauty device cannot be continuously used, with the result that satisfactory effects cannot be obtained; users who have sensitive skin cannot use the beauty device.

In view of the foregoing problems in the conventional techniques, the present invention is created, and an object thereof is to provide a beauty device which is realized by changing a frequency while a voltage or the like is kept constant in order to adjust the degree of a bodily sensation and a control method therefor.

Solution to Problem

In order to solve the problems described above, the present invention provides beauty devices as described below.

Specifically, according to a first embodiment of the present invention, a beauty device is provided that applies an alternating current to the skin surface of a user, and that includes: an electrode portion including two or more electrodes and applying the alternating current between the electrodes; a frequency setting portion setting the frequency of the alternating current either in multiple stages of three or more stages or steplessly; a sensitivity adjusting portion adjusting the degree of a bodily sensation of the user; and an alternating current generating portion outputting the set frequency, and the frequency setting portion sets the frequency based on the adjustment of the sensitivity adjusting portion so as to adjust sensitivity.

According to a second embodiment of the present invention, it is possible to provide the beauty device in which the frequency includes at least a range of 70 KHz to 300 kHz.

According to a third embodiment of the present invention, it is possible to provide the beauty device in which the sensitivity adjusting portion includes an adjustment means allowing the user to arbitrarily perform the adjustment.

According to a fourth embodiment of the present invention, it is possible to provide the beauty device which includes a resistance value measuring portion measuring the resistance value of the skin surface of the user, and in which at least one of configurations is adopted, one of the configurations is that the frequency setting portion performs an adjustment according to a predetermined rule so as to correspond to the adjustment of the sensitivity adjusting portion and the resistance value and the other of the configurations is that the sensitivity adjusting portion is not included and that the frequency setting portion performs an adjustment according to a predetermined rule so as to correspond to the resistance value.

According to a fifth embodiment of the present invention, it is possible to provide the beauty device that includes a heater warming the skin surface.

According to a sixth embodiment of the present invention, it is possible to provide a method for controlling a beauty device applying an alternating current to the skin surface of a user, and while a voltage or a current is kept substantially constant, the frequency of the alternating current is set either in multiple stages of three or more stages or steplessly, and the alternating current of the set frequency is applied from an electrode portion so as to adjust the degree of a bodily sensation of the user.

Advantageous Effects of Invention

In the present invention, it is possible to adjust the degree of a bodily sensation by changing a frequency while a voltage or the like is kept constant, and thus it is possible to provide electrical stimulation of optimal intensity to users who have sensitive skin. In this way, an effective muscle exercise is performed, and an improvement in sagging is provided.

BRIEF DESCRIPTION OF THE DRAWINGS

FIG. 3A shows the waveform of an alternating current in the conventional method, and FIG. 3B shows the waveform of an alternating current in the present invention;

Figure 1:
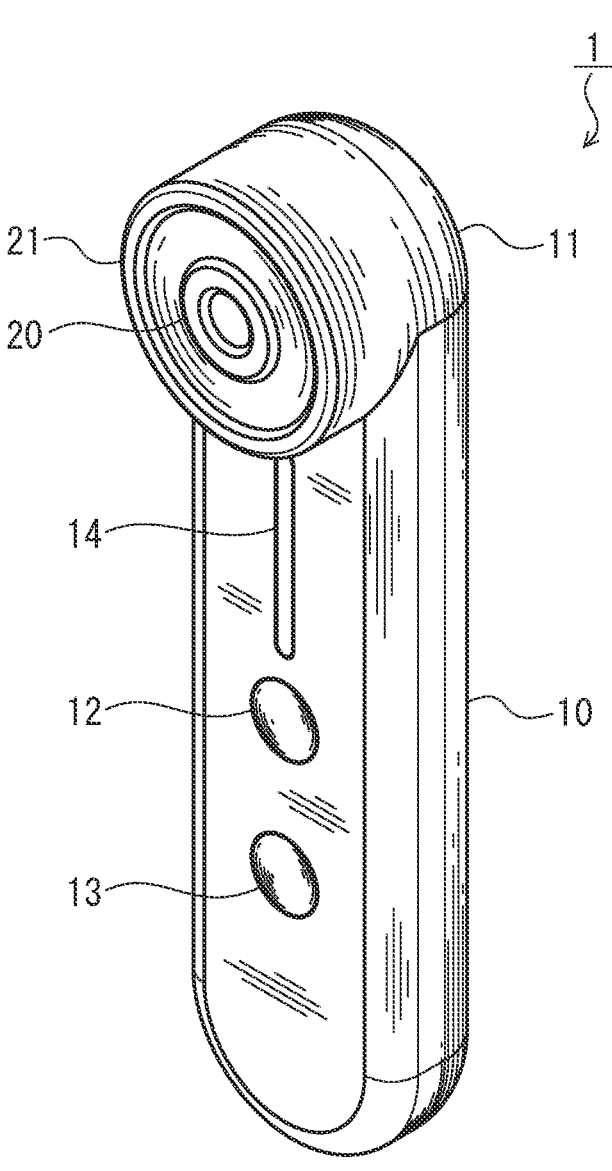
FIG. 1 is a perspective view of a beauty device according to the present invention.

REFERENCE SIGNS LIST 1 beauty device
10 main body portion 11 head portion
12 level switch
13 power supply switch
14 indicator
20 electrode portion
21 electrode portion
30 control substrate
31 electrode portion
32 sensitivity adjusting portion
33 battery
34 frequency setting portion
35 alternating current generating portion
36 resistance value measuring portion

DETAILED DESCRIPTION OF THE EMBODIMENTS

An embodiment of the present invention will be described below based on an example shown in drawings. The present invention is not limited to the embodiment described below.

Figure 2:
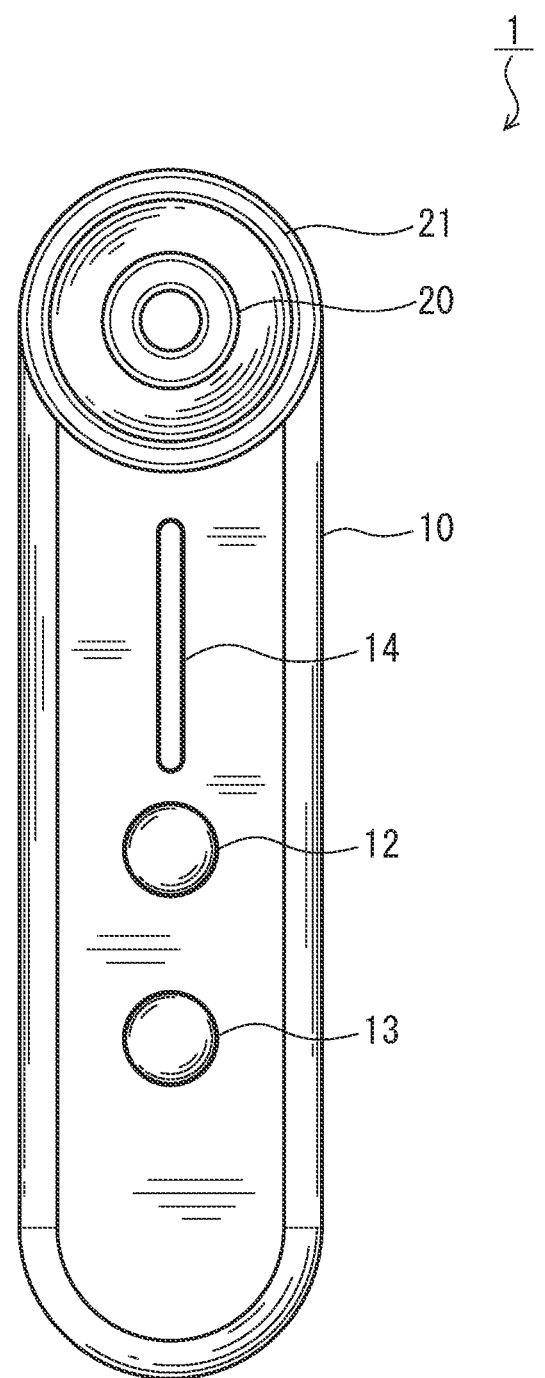
FIG. 2 is a front view of the beauty device according to the present invention.

FIGS. 1 and 2 are a perspective view and a front view of a beauty device (1) according to the present invention. The beauty device (1) is formed with a main body portion (10) which is grasped by a user with a hand and a head portion (11) which includes electrodes. The main body portion (10) includes a level switch (12) for adjusting the degree of a bodily sensation, a power supply switch (13) for switching turning on and off of power and modes, an indicator (14) which indicates the state of a main body and the like.

Although in the main body portion (10), a rechargeable battery is provided and can be used by being charged through power feeding from a power feeding terminal provided in a bottom surface or by feeding power, there is no limitation on whether or not a charging function is provided and a method for feeding power.

In the head portion (11), two annular electrode portions (20) and (21) are provided, and the user brings the head portion (11) into contact with a skin surface and applies an alternating current between the electrode portion (20) in the center and the electrode portion (21) on the edge to be able to achieve beauty effects such as electrical stimulation.

Although in the present invention, this configuration is not necessary, it is also possible to achieve a hyperthermic effect on a skin surface by applying an alternating current in a relatively higher frequency band.

Since electrical muscle stimulation called EMS and a hyperthermic effect using RF (radio frequency) are known, the description of the principles thereof will be omitted.

The configuration of the beauty device described above can freely be changed. Not only the shape of the main body but also the form, the shape and the like of the electrode portions are not limited at all.

Figure 3A:
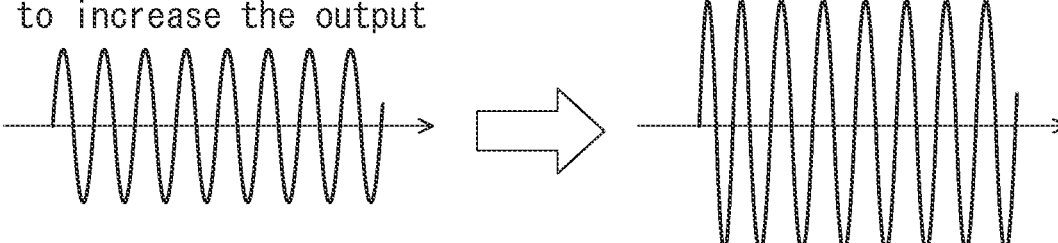
FIGS. 3A-3B provide an illustrative view of a method for controlling the beauty device according to the present invention.

A conventional beauty device is realized by changing a voltage while the frequency of an alternating current is kept constant when the degree of EMS is adjusted. FIG. 3A shows an image of the waveform of a conventional alternating current, and the amplitude (voltage) is increased, and thus the degree of stimulation is increased.

Figure 3B:
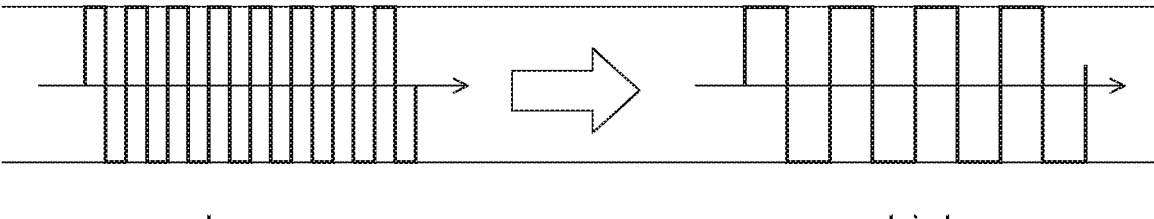

On the other hand, as shown in FIG. 3B, the present invention proposes that the degree of stimulation is adjusted by changing a frequency while a voltage is kept constant.

Although as in the description on the conventional techniques, the technique for changing the frequency is conventionally known, the purpose thereof is to switch between the EMS and the RF. Specifically, in the EMS, an alternating current in a frequency band of several Hz to several kHz is applied, and when the EMS is switched to the RF, the frequency band is changed to a frequency band of several hundred kHz or more. Hence, in order to switch the modes for beauty effects, it is preferable to make a change between the low frequency and the high frequency in two stages.

In addition to the switching of the modes, in order to adjust the degree of stimulation, for example, a voltage can be changed from 40V to 80V. Since how the user feels stimulation differs depending on the characteristics and sensation of the skin, the user brings the beauty device into contact with the skin surface to attempt electrical stimulation, and when a muscle exercise is not sufficient, an operation of increasing the voltage is performed. Although it is possible to change the level of a bodily sensation in this way, when the voltage is increased, the muscle exercise is activated but tingling discomfort is disadvantageously caused.

Hence, the present inventor has found that it is possible to use the change of a frequency in order to adjust the degree of stimulation, and has conducted further research to provide the range of frequencies necessary for the adjustment.

When the frequency is first lowered, the muscle exercise is activated, and the degree of the bodily sensation is increased. By contrast, when the frequency is increased, the muscle exercise is gradually reduced, and the hyperthermic effect is enhanced. In particular, as a result of an experiment using a plurality of testers, it has been found that a boundary between electrical stimulation and hyperthermic action is present between 70 kHz and 300 kHz in the range of high and intermediate frequencies.

Although there are differences depending on the subjects, the hyperthermic action is reduced around or below 70 kHz, and only the electrical stimulation is caused. As the frequency is further lowered, the degree of the bodily sensation is increased. Around 300 kHz, the electrical stimulation is reduced, and the hyperthermic effect is enhanced. Although in the present invention, it is not necessary to cause the hyperthermic effect, as a range for additionally causing the hyperthermic action, it is preferable that a lower limit value be about 100 kHz and that an upper limit value be about 200 kHz. In other words, the range of change in the frequency in the present invention may be set in a range of about 100 kHz to about 200 kHz.

In the characteristics found in the research of the inventor, in a range of 70 kHz to 300 kHz, for people who are unlikely to feel the bodily sensation, it is preferable to lower the frequency to increase the electrical stimulation, and for people who easily feel the bodily sensation, the frequency is increased to reduce the electrical stimulation, the bodily sensation is changed without change of the voltage and thus it is possible to obtain an enhanced bodily sensation without tingling being caused.

In the present invention, the voltage is preferably in a range of 40V to 80V. In the experiment conducted by the present inventor et al., it has been confirmed that when the voltage is set equal to or greater than 80V, discomfort is increased depending on users. The voltage for comfortably providing appropriate electrical stimulation is in a range of 40V to 80V, and is particularly preferably about 60V.

In particular, the range of the frequency described above provides effects in the voltage range described above.

Figure 4:
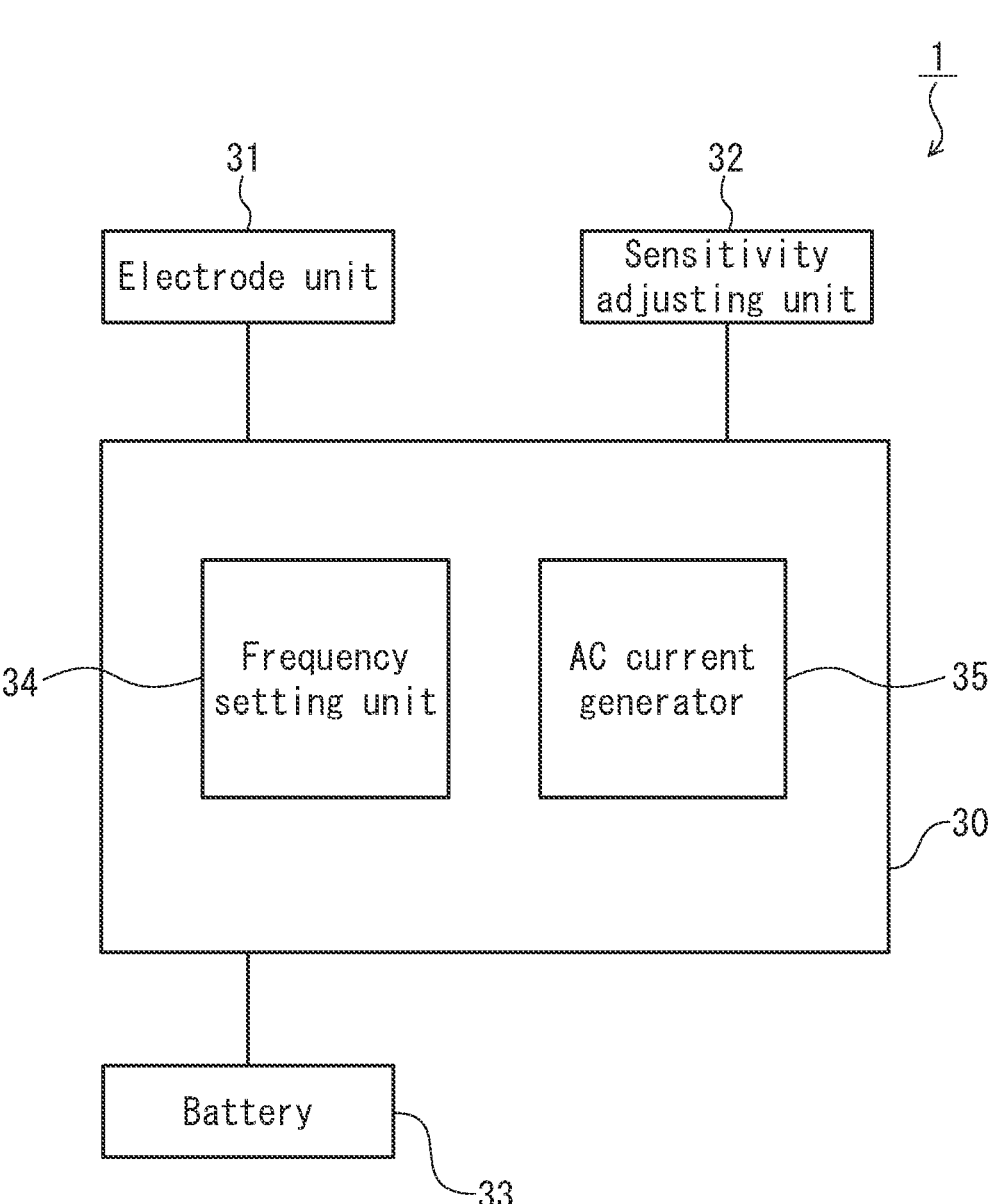
FIG. 4 is a configuration view of the beauty device according to the present invention.

A configuration view of the beauty device (1) according to the present invention is shown in FIG. 4.

In the beauty device (1), a control substrate (30) formed with an electrical circuit or a computer, an electrode portion (31) connected to the control substrate (30), a sensitivity adjusting portion (32), a battery (33) and the like are arranged. The control substrate includes a frequency setting portion (34) which sets the frequency of the alternating current either in multiple stages of three or more stages or steplessly and an alternating current generating portion (35) which outputs the set frequency.

The electrode portion (31) includes two or more electrodes and applies the alternating current between the electrodes. The sensitivity adjusting portion (32) uses, for example, a switch of a button type such as the level switch (12) shown in FIG. 1 or a dial type so as to adjust the degree of the bodily sensation of the user. The battery (33) is a rechargeable battery or a dry battery or may be replaced with a solar panel or an external power supply.

Conventionally, it is technically difficult to change a frequency due to the ability of the CPU of the computer forming the control substrate. For example, in a CPU in which the number of clocks is about 4 MHz, the frequency of an alternating current formed by software is limited to about 1 kHz, and thus an oscillator circuit with a fixed constant is provided for switching the frequencies.

However, since in recent years, even a CPU in which the number of clocks is 32 MHz or the like has been able to be used inexpensively, it is possible to generate, only by software, an alternating current of a high frequency such as 100 kHz or 1 MHz.

Conventionally, in the technical background as described above, it is not assumed that a frequency can be changed in small-sized devices such as a beauty device. However, with the progress of CPUs, the present invention can easily be realized.

Hence, in the present invention, the frequency of the alternating current set by the frequency setting portion (34) of the CPU can be output as the alternating current from the alternating current generating portion (35) realized by software. In order to produce a digital output, as shown in FIG. 3B, a rectangular wave is output in the present example.

Since in the present invention, a method for generating the alternating current is not limited, an oscillator circuit whose frequency can be changed may be provided. The waveform may be a sinusoidal wave or a pseudo sinusoidal wave.

A specific control method will be described.

The user performs the operation of the sensitivity adjusting portion (32) serving as an adjustment means to set the desired intensity of electrical stimulation. For example, when power is turned on, the intensity is set to the lowest level. Here, the frequency setting portion (34) sets the frequency to 300 kHz, and thus the alternating current generating portion (35) generates the alternating current of 300 KHz.

When the degree of the bodily sensation is low, the sensitivity adjusting portion (32) is operated to increase the degree, and thus the frequency setting portion sequentially sets the frequency low. It is also possible to stepwise set frequencies, and for example, when three stages are provided, three frequencies of 70 kHz, 150 kHz and 300 kHz are used, and when eight stages are provided, frequencies of 70 kHz, 90 kHz, 120 kHz, 150 kHz, 180 kHz, 220 kHz, 260 kHz and 300 kHz are used.

In a case where the lower limit value of the variable range is set to 100 kHz and the upper limit value is set to 200 kHz, it is also possible to stepwise set frequencies, and for example, when three stages are provided, three frequencies of 100 kHz, 150 kHz and 200 kHz are used, and when eight stages are provided, frequencies of 100 kHz, 110 kHz, 120 kHz, 130 kHz, 140 kHz, 160 kHz, 180 kHz and 200 kHz are used.

A configuration may be adopted in which in order to further increase the degree of the bodily sensation, it is possible to change to a frequency band of several Hz to several kHz.

Since in the beauty device (1) of the present example, only the hyperthermic effect of RF is provided, the frequency band may be changed to a higher frequency band.

In the present invention, in addition to the operation of the sensitivity adjusting portion (32) performed by the user, the setting of the frequency can be automated. The resistance value of a skin surface is a cause of an influence on the bodily sensation of the user, as shown in FIG. 4, the control substrate (30) includes a resistance value measuring portion (36), energization is performed in the electrode portion (31) and thus the resistance value of the skin is measured. Another electrode for the resistance measurement may be provided.

The frequency setting portion (34) sets, according to the measured resistance value, a frequency corresponding to the characteristics of the skin. For example, the setting is made as in table 1 below.

TABLE 1

| Resistance value | Frequency |
| --- | --- |
| less than 10 kΩ | 300 kHz |
| 10 kΩ to 500 kΩ | 120 kHz |
| more than 500 kΩ | 70 kHz |

In the table above, when the resistance value is relatively low, the current easily flows to increase the degree of the bodily sensation, and thus the frequency is set high. When the resistance value is relatively high, the current is unlikely to flow to reduce the degree of the bodily sensation, and thus the frequency is set low.

Since the resistance value of the skin of the same person changes depending on moisture and the degree of moistness of the skin, even when the adjustment is performed with the level switch in the same manner, the degree of a bodily sensation changes depending on the timing. Hence, the adjustment is automatically performed based on the result of the measurement made by the frequency setting portion (34), and thus the beauty device can be used every time with the same sensation.

Figure 5:
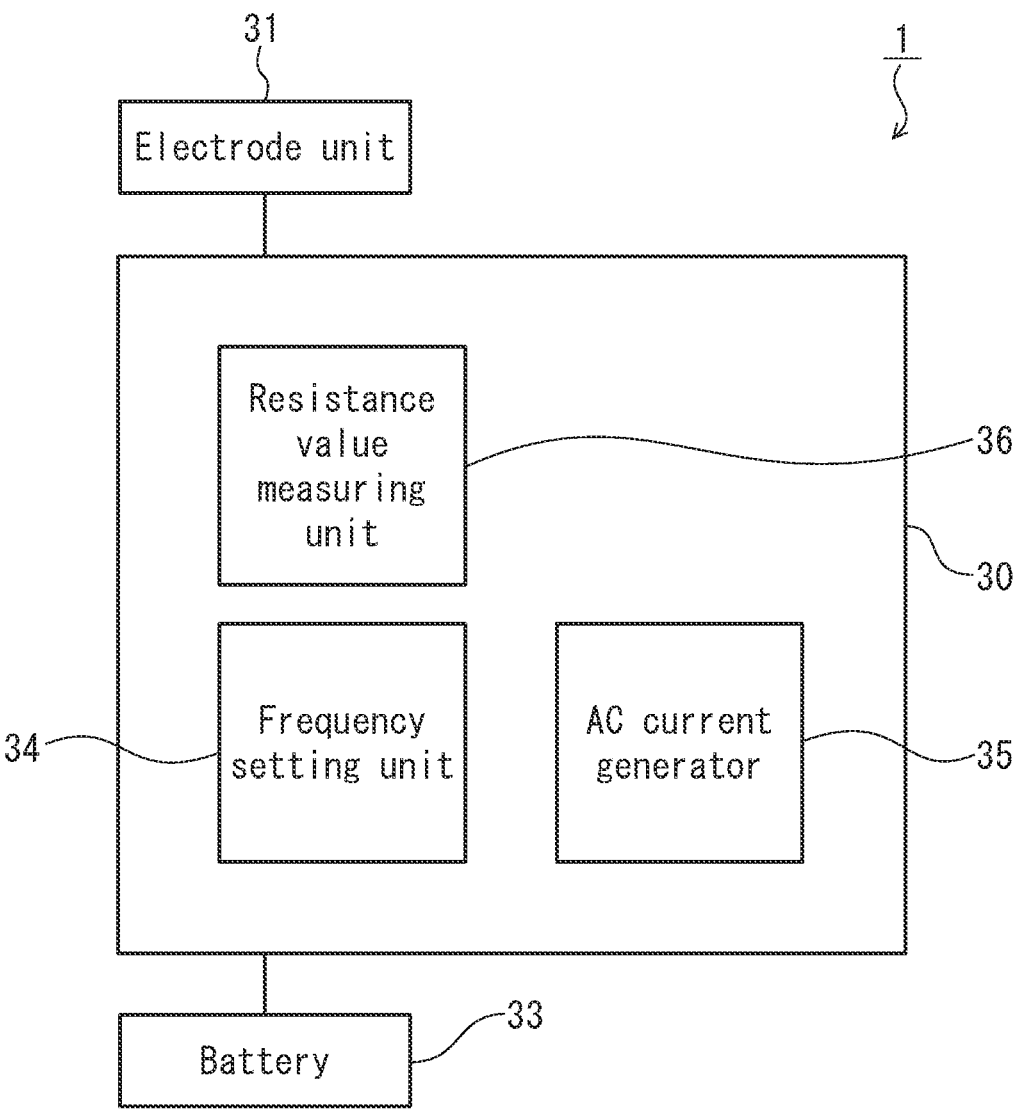
FIG. 5 is a configuration view of a beauty device according to another example of the present invention.

Although in the configuration of FIG. 5, the sensitivity adjusting portion (32) is omitted, for example, the sensitivity adjusting portion (32) may be included to switch between a low level, an intermediate level and a high level. In this case, with the sensitivity adjusting portion (32), as in table 2 below, the resistance value and the setting of the user are combined together, and thus the frequency can also be set.

TABLE 2

| Resistance value | Frequency (low) | Frequency (intermediate) | Frequency (high) |
| --- | --- | --- | --- |
| less than 10 kΩ | 300 kHz | 200 kHz | 150 kHz |
| 10 kΩ to 500 kΩ | 150 kHz | 160 kHz | 100 kHz |
| more than 500 kΩ | 100 kHz | 80 kHz | 70 kHz |

As described above, the frequency setting portion (34) sets the optimal frequency according to the measured value of the resistance value measuring portion (36), and thus the user can easily use the beauty device.

The values in the table above are an example, and the values of the frequency, the steps of switching and the like can be arbitrarily changed. A rule for setting the frequency may be based not on the table but on the result of a calculation using a predetermined calculation formula.

The beauty device (1) of the present invention can further include a heater (not shown).

Examples of the heater include a ceramic Peltier heater for generating far infrared rays and the like, and a deep portion of the skin can be warmed.

In the frequency band of the present invention from 70 kHz to 300 kHz, at frequencies around a range of 200 kHz to 300 kHz where the user easily feels hyperthermic action, an area around the epidermis of the skin surface is warmed. In addition, the heater is used, and thus dermis which is a deep portion is warmed, with the result that the beauty device can be made to act on the skin with low stimulation and effectively.

Since in a range on the side of low frequencies, it is likely that the user easily feels electrical stimulation but is unlikely to feel hyperthermic action, the heater is additionally used, and thus it is possible to make the adjustment to user's favorite hyperthermic action, with the result that it is particularly effective to use the heater together with the technique for adjusting the frequency in the present invention.

The present invention can provide not only the beauty device described above but also a method for controlling a beauty device which applies an alternating current to the skin surface of the user.

Specifically, while a voltage or a current is kept substantially constant, the frequency of the alternating current is set either in multiple stages of three or more stages or steplessly, and the alternating current of the set frequency is applied from an electrode portion so as to adjust the degree of the bodily sensation of the user.

A specific method is illustrated in the above description of the beauty device (1), and in particular, it is obvious that the method is performed by combining the control substrate (30), the electrode portion (31) and the sensitivity adjusting portion (32). However, there is no limitation on this method. A device which incorporates the present control method is not limited to a portable beauty device, and may be a stationary device.

What is claimed is:

1. A beauty device for applying an alternating current to a skin surface of a user, comprising: an electrode portion, including two or more electrodes and configured for applying alternating current between the two or more electrodes; a frequency setting portion for setting a set frequency of the alternating current either in three or more stages or steplessly; a sensitivity adjusting portion to set a desired degree of bodily tingling sensation, the sensitivity adjusting portion is operable by the user to indicate the desired degree of bodily tingling sensation, wherein the degree of bodily tingling sensation is controlled by adjusting the frequency of the alternating current; and an alternating current generating portion for outputting alternating current having the set frequency wherein the alternating current generating portion is configured to produce alternating current having a constant voltage and rectangular wave output, a heater configured for warming the skin of the user, and a resistance value measuring portion for measuring a resistance value of the skin surface of the user, wherein the frequency setting portion sets the set frequency based on the resistance value, and wherein the set frequency is set in a range of 100 kHz to 300 kHz, and further comprising a control substrate including the frequency setting portion and an alternating current generating portion, and the frequency setting portion sets, according to the measured resistance value, a frequency corresponding to characteristics of the skin, and with the sensitivity adjusting portion the resistance value and a setting of the user are combined together, and wherein the frequency includes at least a range of 70 kHz to 300 kHz, the control substrate being configured to command the alternating current generating portion to update the frequency while maintaining the output voltage constant.

2. A method for controlling a beauty device for applying an alternating current to a skin surface of a user, comprising steps of: contacting the skin surface of the user with an electrode portion and resistance value measuring portion of a beauty device, and wherein during applying alternating current the voltage is kept constant, the alternating current having a rectangular wave output, a set frequency of the alternating current is set either in multiple stages of three or more stages or steplessly, and the alternating current having the set frequency is applied from the electrode portion to the skin surface of the user so as to control a degree of bodily tingling sensation of the user, and wherein the set frequency is set in a range of 100 kHz to 300 kHz, measuring a resistance value of the skin surface of the user; receiving a user input indicating a desired degree of bodily tingling sensation; mapping combinations of measured skin resistance value ranges and user-selected tingling sensation levels to discrete frequency values within 100 kHz to 300 kHz to determine a set frequency; and commanding an alternating current generating portion to output alternating current at the set frequency while keeping the output voltage constant and the alternating current having a rectangular wave output.

* * * * *